(12) United States Patent
Shin et al.

(10) Patent No.: US 11,684,317 B2
(45) Date of Patent: Jun. 27, 2023

(54) DISEASE PREDICTION MODEL CONSTRUCTION APPARATUS AND METHOD, AND DISEASE PREDICTION APPARATUS

(71) Applicant: SAMSUNG ELECTRONICS CO., LTD., Suwon-si (KR)

(72) Inventors: Eui Seok Shin, Yongin-si (KR); Jin Young Park, Hwaseong-si (KR); Seung Jun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 372 days.

(21) Appl. No.: 16/919,944

(22) Filed: Jul. 2, 2020

(65) Prior Publication Data

US 2020/0330048 A1 Oct. 22, 2020

Related U.S. Application Data

(62) Division of application No. 15/237,012, filed on Aug. 15, 2016, now Pat. No. 10,729,383.

(30) Foreign Application Priority Data

Nov. 16, 2015 (KR) ......................... 10-2015-0160724

(51) Int. Cl.
*A61B 5/1455* (2006.01)
*A61B 5/00* (2006.01)
(Continued)

(52) U.S. Cl.
CPC .......... *A61B 5/7275* (2013.01); *A61B 5/1455* (2013.01); *A61B 5/14532* (2013.01);
(Continued)

(58) Field of Classification Search
CPC . A61B 5/7275; A61B 5/14532; A61B 5/1455; A61B 5/4848; A61B 5/7246; A61B 5/7405
See application file for complete search history.

(56) References Cited

U.S. PATENT DOCUMENTS 6,493,566 B1 * 12/2002 Ruchti ................. A61B 5/0059
600/309
7,043,288 B2 * 5/2006 Davis, III ............ A61B 5/0059
600/310
(Continued)

FOREIGN PATENT DOCUMENTS

DE 10 2006 026 173 A1 12/2007
JP 2004-73814 A 3/2004
(Continued)

OTHER PUBLICATIONS

Sakaguchi et al., "Glucose area under the curve during oral glucose tolerance test as an index of glucose intolerance", May 14, 2015, 6 pages total, The Japan Diabetes Society.

*Primary Examiner* — Marjan Fardanesh
(74) *Attorney, Agent, or Firm* — Sughrue Mion, PLLC

(57) ABSTRACT

A disease prediction model construction apparatus is provided. The disease prediction model construction apparatus may include a spectral data acquisition unit that emits near-infrared rays toward a skin of a subject to acquire near-infrared spectral data and a prediction model construction unit that constructs a disease prediction model based on a time-blood glucose graph generated from the acquired near-infrared spectral data.

6 Claims, 13 Drawing Sheets

(51) Int. Cl.
*G16H 50/50* (2018.01)
*G16H 50/20* (2018.01)
*A61B 5/145* (2006.01)

(52) U.S. Cl.
CPC .......... *A61B 5/4848* (2013.01); *A61B 5/7246* (2013.01); *A61B 5/742* (2013.01); *A61B 5/7405* (2013.01); *A61B 5/7455* (2013.01); *G16H 50/20* (2018.01); *G16H 50/50* (2018.01); *A61B 5/7203* (2013.01); *A61B 5/7253* (2013.01)

(56) References Cited

U.S. PATENT DOCUMENTS

| | | |
|---|---|---|
| 7,133,710 B2 | 11/2006 | Acosta et al. |
| 2005/0148834 A1 | 7/2005 | Hull et al. |
| 2013/0004972 A1 | 1/2013 | Watanabe |
| 2014/0353503 A1 | 12/2014 | Lanan et al. |

FOREIGN PATENT DOCUMENTS

| | | | |
|---|---|---|---|
| JP | 2004-229973 A | 8/2004 |
| JP | 2005-519682 A | 7/2005 |
| JP | 2007-181602 A | 7/2007 |
| JP | 2011-154018 A | 8/2011 |
| KR | 10-0775669 B1 | 11/2007 |
| KR | 10-0917079 B1 | 9/2009 |

\* cited by examiner

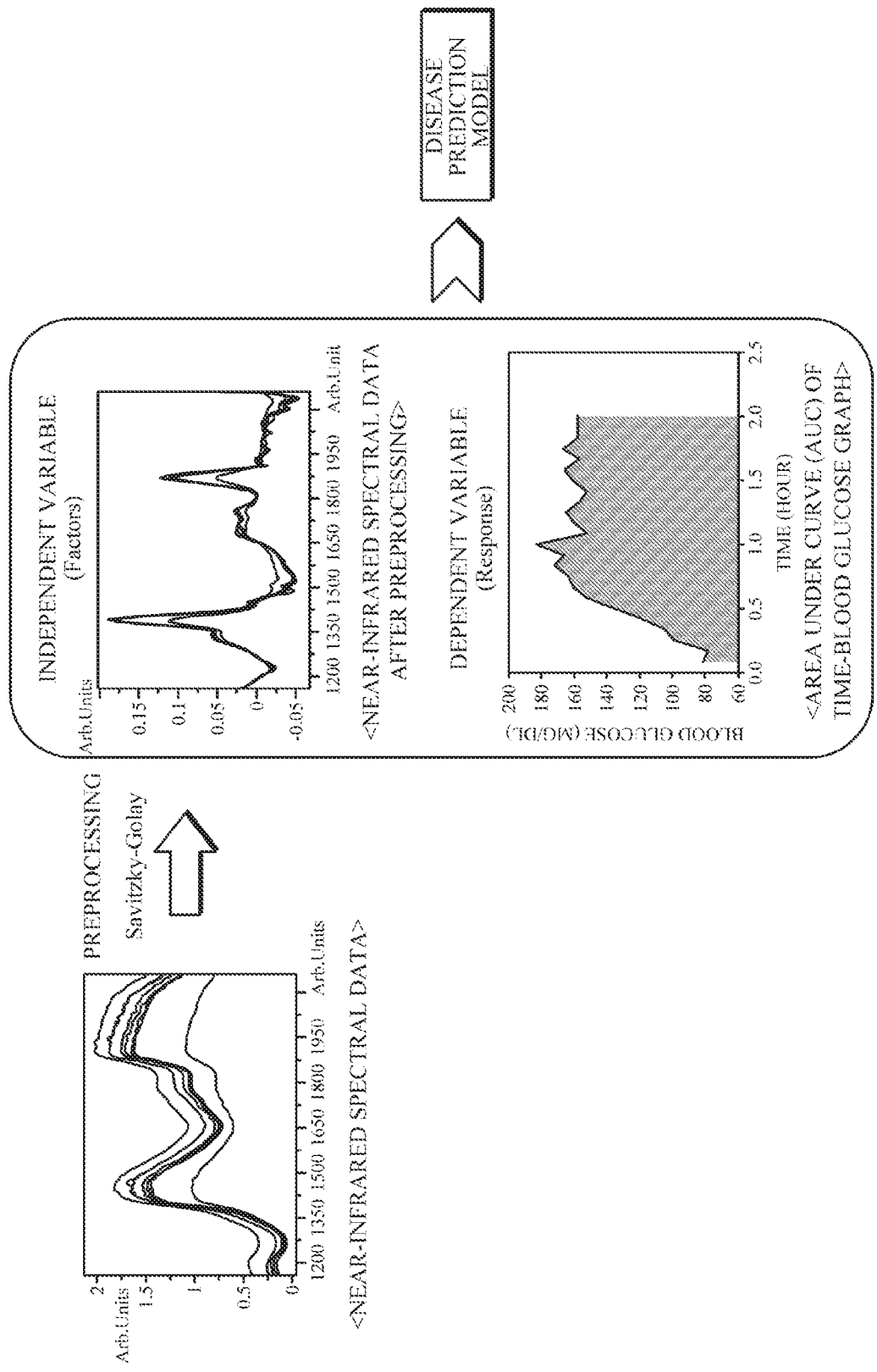

DISEASE PREDICTION MODEL CONSTRUCTION APPARATUS AND METHOD, AND DISEASE PREDICTION APPARATUS

CROSS-REFERENCE TO RELATED APPLICATION

This application is a divisional application of U.S. application Ser. No. 15/237,012, filed Aug. 15, 2016, which claims priority from Korean Patent Application No. 10-2015-0160724, filed on Nov. 16, 2015 in the Korean Intellectual Property Office, the disclosures of which are herein incorporated by reference in their entireties.

BACKGROUND

1. Field

Apparatuses and methods consistent with exemplary embodiments relate to a disease prediction technology, and more particularly to a disease prediction model construction apparatus and method and a disease prediction apparatus.

2. Description of Related Art

Diabetes is one of the chronic diseases of modern people. The diabetes is diagnosed when an insulin hormone is not properly secreted from a pancreas or does not correctly function to regulate glucose level in blood. Due to the dysfunction in insulin action, glucose within blood is not transferred to cells for use as energy and is accumulated in the blood. The diabetes may cause complications such as hypertension, renal failure, or impaired vision.

An impaired glucose tolerance corresponding to prediabetes is a symptom that occurs in a pre-step of Type 2 diabetes that is a diabetes disease caused by insulin resistance and is a state in which a blood glucose concentration increased due to abnormality of a glucose metabolism. A method of diagnosing impaired glucose tolerance includes an invasive method of collecting blood and measuring blood glucose that changes over time through a glucose tolerance test. However, there are pain and inconvenience of blood collection using a needle, a high risk of infection of a disease, and a large economic burden due to use of consumables such as a body fluid component measurement strip or a needle.

Accordingly, a non-invasive method of diagnosing an impaired glucose tolerance has been studied. In the non-invasive method, a fluorescence spectrum of skin is measured, and the amount of glycated protein advanced glycation end (AGE) product in the skin is estimated for predicting a glucose metabolism disorder. When a state of high concentration glucose is continually maintained, proteins distributed in blood vessels and tissues are glycated due to a non-enzymatic reaction, and the glycated proteins emit fluorescence when irradiated with ultraviolet rays. This means that an increased amount of the fluorescence emitted due to irradiation of the skin with the ultraviolet rays indicates an increase of the glycated protein. Through the increase in the glycated protein, a level of the glucose metabolism disorder is predicted.

For fluorescence spectroscopy, it may be necessary to irradiate skin with ultraviolet rays A (UVA) in a region of 320 nm to 380 nm and measure a fluorescence signal that is emitted from the skin due to the ultraviolet rays. However, when the skin is irradiated with the UVA, photo-aging of skin tissue is promoted, DNA damage and immunosuppression of the skin tissue are caused, and thus, a likelihood of skin cancer is increased.

SUMMARY

According to an aspect of an exemplary embodiment, there is provided a disease prediction model construction apparatus including: a spectral data acquisition unit that emits near-infrared rays toward a skin of a subject to acquire near-infrared spectral data; and a prediction model construction unit that constructs a disease prediction model based on a time-blood glucose graph generated from the acquired near-infrared spectral data.

The disease prediction model may analyze an impaired glucose tolerance of the subject.

The disease prediction model construction apparatus may further include a preprocessing unit that removes noise from the acquired near-infrared spectral data.

The preprocessing unit may use a Savitzky-Golay filter algorithm to remove the noise from the acquired near-infrared spectral data.

The disease prediction model construction apparatus may further include a blood glucose change measurement unit that measures a change in blood glucose of the subject for a predetermined time after the subject takes glucose in a fasting state; and a time-blood glucose graph generation unit that generates the time-blood glucose graph based on the measured change in the blood glucose.

The prediction model construction unit may calculate an area under a curve (AUC) from the generated time-blood glucose graph and construct the disease prediction model based on a correlation between the acquired near-infrared spectral data and the calculated area under the curve.

The prediction model construction unit may determine the correlation by using the acquired near-infrared spectral data as an independent variable of a predefined regression analysis algorithm and using the calculated area under the curve as a dependent variable.

The regression analysis algorithm may be one of a partial least square regression algorithm, a principal components regression algorithm, and a multivariate regression algorithm.

Further, the disease prediction model construction apparatus may further include a feature information input unit that receives at least one of sex, age, height, and body weight of the subject as feature information, and the prediction model construction unit may construct the disease prediction model based on the input feature information of the subject.

According to an aspect of another exemplary embodiment, there is provided a disease prediction model construction method including: emitting near-infrared rays toward a skin of a subject to acquire near-infrared spectral data; and constructing a disease prediction model based on a time-blood glucose graph generated from the acquired near-infrared spectral data.

The disease prediction model may analyze an impaired glucose tolerance of the subject.

The method for constructing a disease prediction model may further include: measuring a change in blood glucose for a predetermined time after the subject takes glucose of the subject in a fasting state; and generating the time-blood glucose graph based on the measured change of the blood glucose.

The constructing the disease prediction model may include: calculating an area under a curve (AUC) from the generated time-blood glucose graph; and constructing the disease prediction model based on a correlation between the acquired near-infrared spectral data and the calculated area under the curve.

The constructing the disease prediction model may include determining the correlation by using the acquired near-infrared spectral data as an independent variable of a predefined regression analysis algorithm and by using the calculated area under curve as a dependent variable.

According to an aspect of another exemplary embodiment, there is provided a disease prediction apparatus including: a spectral data acquisition unit that emits near-infrared rays toward a skin of a subject to acquire near-infrared spectral data; and a prediction unit that applies a disease prediction model to the acquired spectral data of the subject and predicts disease of the subject.

The prediction unit may estimate an area under a curve (AUC) of a time-blood glucose graph generated from the acquired near-infrared spectral data based on the disease prediction model and predict the disease as prediabetes when the estimated area under the curve is greater than or equal to a threshold value.

The disease prediction apparatus may further include a result providing unit that provides information of the predicted disease to the subject.

BRIEF DESCRIPTION OF THE DRAWINGS

The above and/or other aspects will be more apparent by describing certain exemplary embodiments, with reference to the accompanying drawings, in which:

FIG. 4 is an illustrative diagram illustrating a process of establishing a disease prediction model according to an exemplary embodiment.

DETAILED DESCRIPTION

Figure 1:
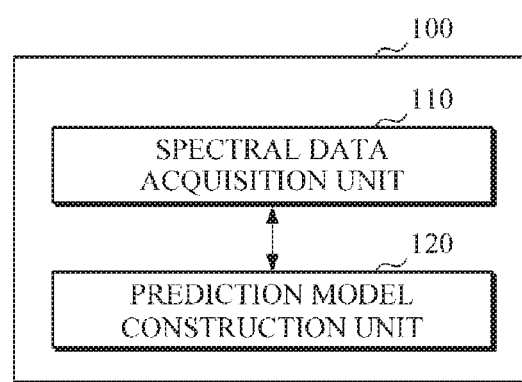
FIG. 1 is a block diagram illustrating a disease prediction model construction apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list.

As is traditional in the field of the inventive concepts, embodiments are described, and illustrated in the drawings, in terms of functional blocks, units and/or modules. Those skilled in the art will appreciate that these blocks, units and/or modules are physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units and/or modules being implemented by microprocessors or similar, they may be programmed using software (e.g., microcode) to perform various functions discussed herein and may optionally be driven by firmware and/or software. Alternatively, each block, unit and/or module may be implemented by dedicated hardware, or as a combination of dedicated hardware to perform some functions and a processor (e.g., one or more programmed microprocessors and associated circuitry) to perform other functions. Also, each block, unit and/or module of the embodiments may be physically separated into two or more interacting and discrete blocks, units and/or modules without departing from the scope of the inventive concepts. Further, the blocks, units and/or modules of the embodiments may be physically combined into more complex blocks, units and/or modules without departing from the scope of the inventive concepts.

FIG. 1 is a block diagram illustrating a disease prediction model construction apparatus according to an exemplary embodiment. The disease prediction model construction apparatus 100 may include a spectral data acquisition unit (e.g., a light emitter and receiver) 110 and a prediction model construction unit 120. The prediction model construction unit 120 may be implemented by a processor.

The spectral data acquisition unit 110 may emit near-infrared rays to the skin of a subject to acquire near-infrared spectral data that is reflected from the skin. For example, the spectral data acquisition unit 110 may emit the near-infrared rays toward the skin of the subject and sense light that is reflected from the skin to acquire the near-infrared spectral data. In this case, a near-infrared spectral region may have a wavelength range from 1158 nm to 2130 nm but is not limited thereto. Further, a measured part of the subject is not limited to a specific part of a body and may be changed according to convenience and physical condition of the subject.

The spectral data acquisition unit 110 may acquire the near-infrared spectral data of the subject in a measurement.

Alternatively, the spectral data acquisition unit 110 may acquire the near-infrared spectral data in several measurements. In this case, the spectral data acquisition unit 110 may acquire statistical values including an average value, a median value, a minimum value, a maximum value, etc. of a plurality of acquired spectral data as the near-infrared spectral data of the subject. However, the present embodiment is not limited thereto, and each of the measured spectral data items may be weighted and the resultant statistical value may be acquired as the near-infrared spectral data of the subject.

In this case, the number of subjects is not particularly limited. When there is a plurality of subjects, the spectral data acquisition unit 110 may acquire the near-infrared spectral data for each subject.

The prediction model construction unit 120 may construct a disease prediction model for disease prediction using the acquired near-infrared spectral data. In this case, the prediction model construction unit 120 may construct a disease prediction model on the basis of the near-infrared spectral data acquired for the subject and the time-blood glucose graph generated for the subject. Here, the disease may include impaired glucose tolerance which is one of the prediabetes symptoms but is not limited thereto.

For example, the prediction model construction unit 120 may calculate an area under a curve using the time-blood glucose graph generated for the subject and construct the disease prediction model using a correlation between the near-infrared spectral data acquired for the subject and the calculated area under the curve. For example, the prediction model construction unit 120 may input the near-infrared spectral data of the subject and the area under the curve as an independent variable and a dependent variable respectively for a regression analysis algorithm and determine a correlation in a regression analysis model to construct the disease prediction model. In this case, the regression analysis algorithm may include, for example, a partial least square regression algorithm, a principal components regression algorithm, or a multivariate regression algorithm but is not limited thereto.

Figure 2:
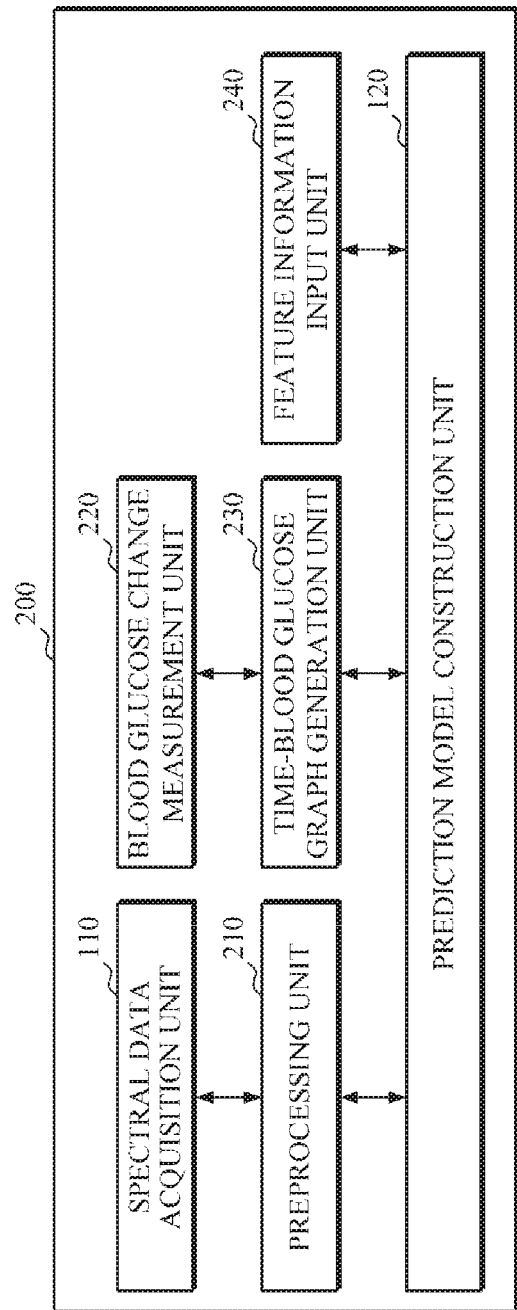
FIG. 2 is a block diagram illustrating a disease prediction model construction apparatus according to another exemplary embodiment.

FIG. 2 is a block diagram illustrating a disease prediction model construction apparatus according to another exemplary embodiment. A disease prediction model construction apparatus 200 may include a spectral data acquisition unit 110, a preprocessing unit 210, a blood glucose change measurement unit 220, a time-blood glucose graph generation unit 230, a feature information input unit 240, and a prediction model construction unit 120. Hereinafter, a different configuration will be mainly described below.

When the near-infrared spectral data are acquired from the subject, the preprocessing unit 210 may preprocess the acquired spectral data to remove noise.

Figure 3A:
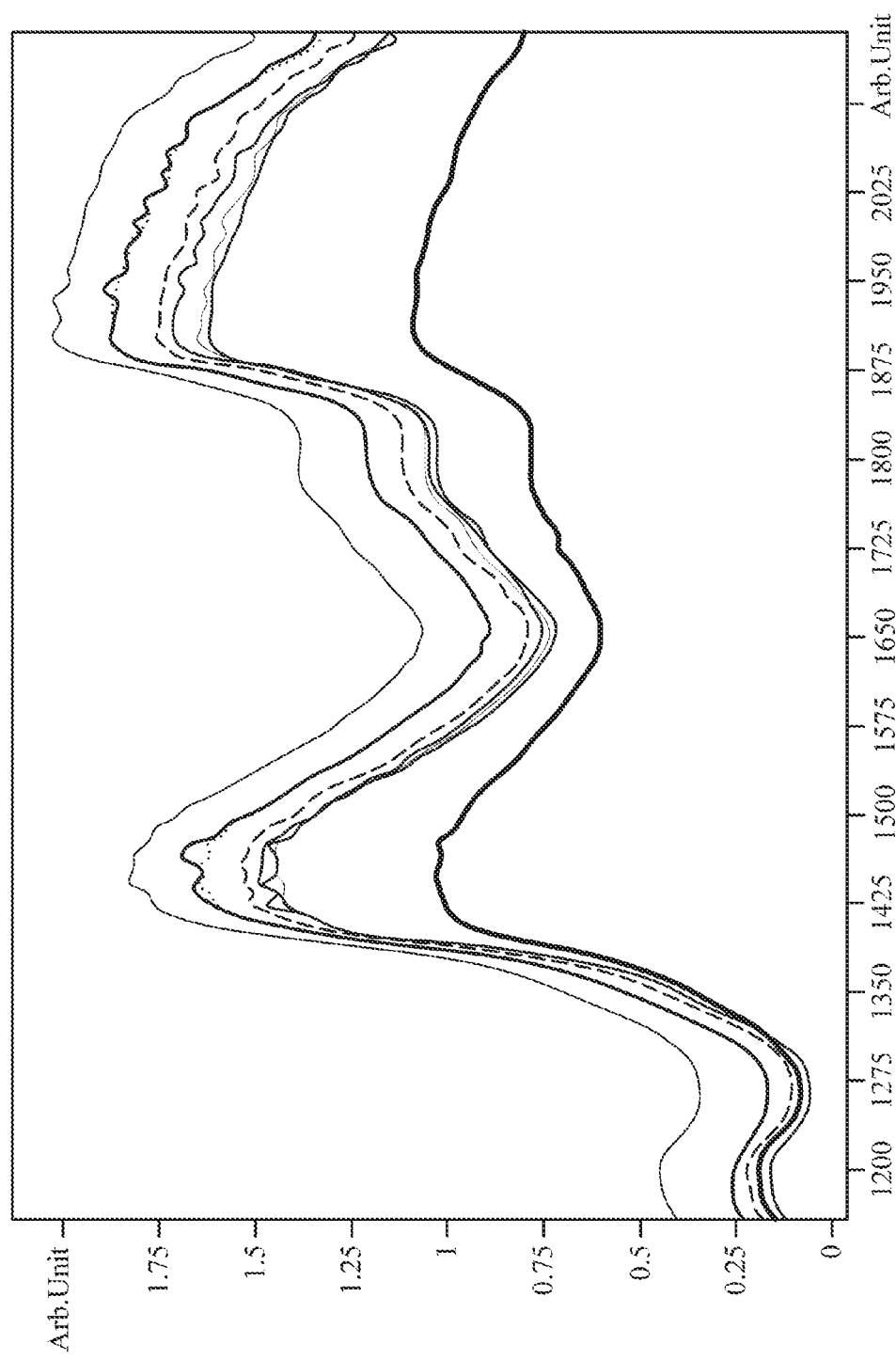
FIG. 3A is an illustrative diagram illustrating near-infrared spectral data of skin of a subject according to an exemplary embodiment.

FIG. 3A is an illustrative diagram illustrating near-infrared spectral data of the skin of the subject according to an exemplary embodiment. As shown in FIG. 3A, spectral data of a plurality subjects are acquired by the spectral data acquiring unit 110 before being preprocessed in the preprocessing unit 210.

Figure 3B:
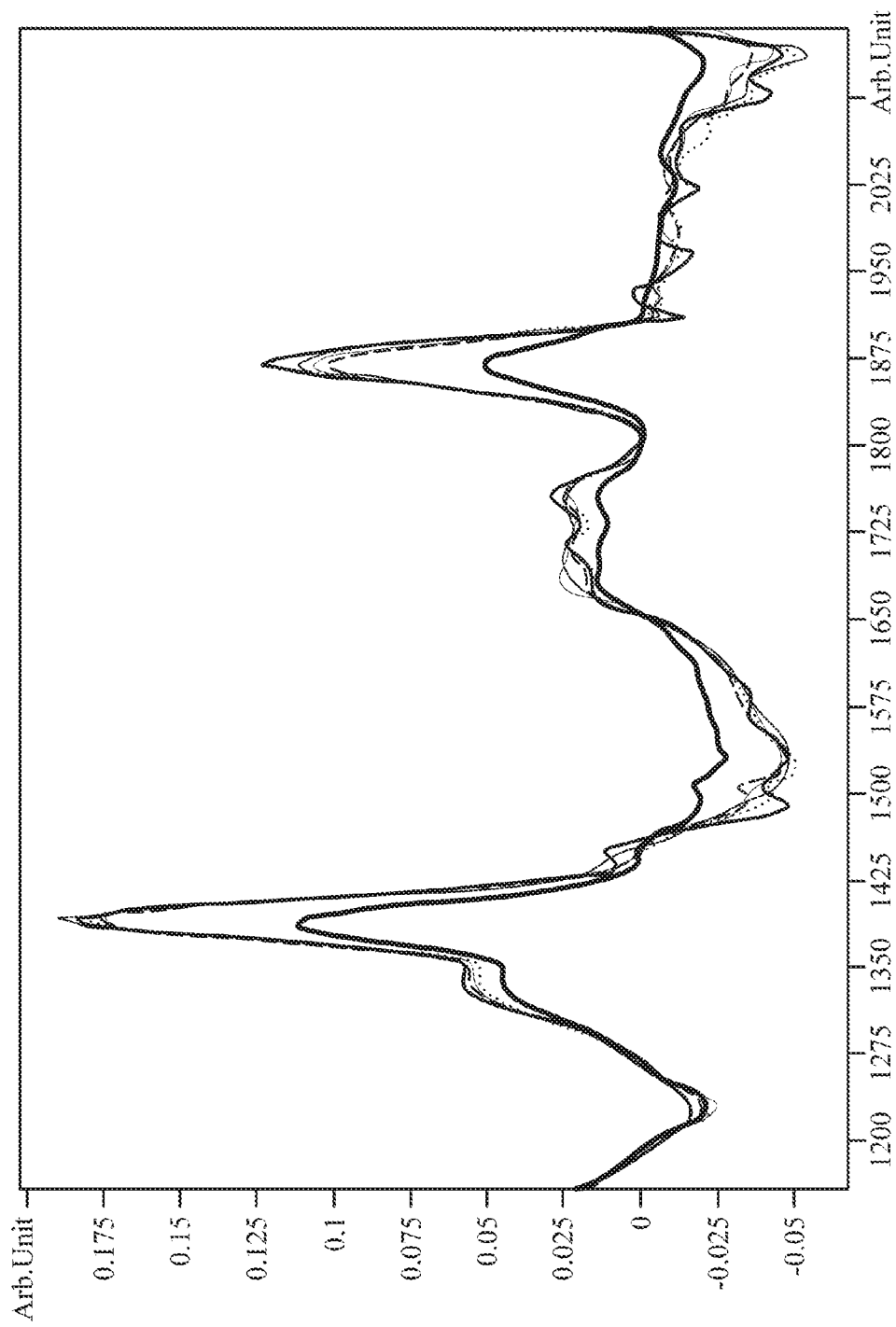
FIG. 3B is an illustrative diagram in which a first-order Savitzky-Golay derivative filter is applied to near-infrared spectral data of skin of a subject according to an exemplary embodiment.

FIG. 3B is an illustrative diagram illustrating a case in which the near-infrared spectral data of the skin of the subject are preprocessed by applying a first-order Savitzky-Golay derivative filter according to an exemplary embodiment. Referring to FIG. 3B, the preprocessing unit 210 may preprocess the near-infrared spectral data of a plurality of subjects illustrated in FIG. 3A and provide the resultant data to the prediction model construction unit 120.

In this case, a preprocessing algorithm may include, for example, a moving average filter, an average value filter, a weighting value filter, and a Savitzky-Golay filter, but the present invention is not limited thereto.

Through the preprocessing process in the preprocessing unit 210, it is possible to remove noise of the acquired spectral data and minimize a deviation according to characteristics of the skin between the subjects and a deviation generated according to measured part.

Referring back to FIG. 2, the blood glucose change measurement unit 220 may measure a change in the blood glucose of the subject for a predetermined time after the subject takes glucose in a fasting state. For example, the blood glucose change measurement unit 220 may measure the change in the blood glucose using a method of tracking a change in a concentration of glucose from the blood collected at certain time intervals for two hours after the subject takes glucose of 75 g in a fasting state. For example, the blood glucose change measurement unit 220 may measure the change in the blood glucose by an oral glucose tolerance test (OGTT).

The time-blood glucose graph generation unit 230 may generate the time-blood glucose graph on the basis of the measured change in the blood glucose. For example, since the concentration of the glucose in the blood immediately after the subject takes the glucose of 75 g varies with time, a blood glucose graph with a change in the time as X-axis and the blood glucose according to time as Y-axis can be obtained by tracking the glucose concentration of the blood collected at certain time intervals according to time.

Figure 3C:
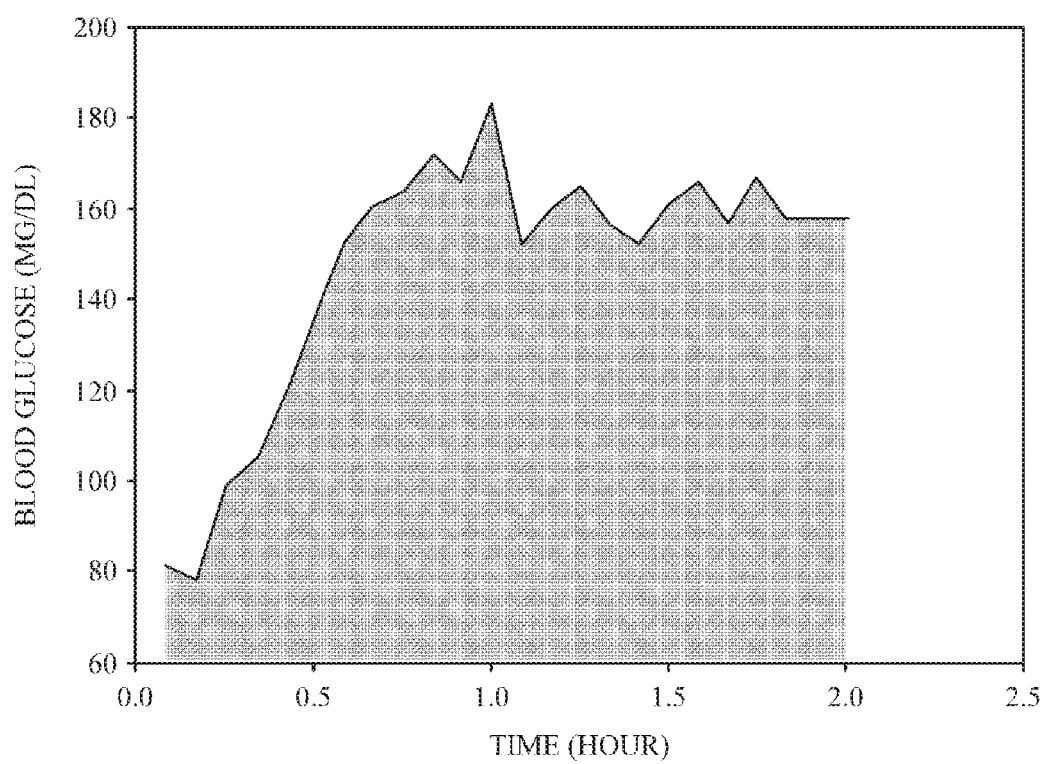
FIG. 3C is an illustrative diagram illustrating a time-blood glucose graph and an area under curve according to an exemplary embodiment.

FIG. 3C is an illustrative diagram illustrating a time-blood glucose graph and an area under a curve according to an exemplary embodiment. A description will be given by way of an example with reference to FIG. 3C. The time-blood glucose graph generation unit 230 may generate a time-blood glucose graph by collecting blood at certain time intervals for two hours after a subject takes glucose of 75 g in a fasting state, tracking a change in a concentration of the glucose from the collected blood, and representing the change on a two-dimensional plane having time (hour) as X-axis and the blood glucose (mg/dl) according to time as Y-axis.

The prediction model construction unit 120 may calculate the area under the curve from the time-blood glucose graph. In this case, the area under the curve indicates an area (mg·h/dl) of a portion surrounded by a curve drawn in the time-blood glucose graph, the X-axis (time), the Y-axis (blood glucose), and a straight line (X=t) for an arbitrary time t. For example, the area under the curve y=f(x) between x=a and x=b may be obtained by integrating y=f(x) between the limits of a and b. Here, the values of a and b may be set as 0.0 and 2.0 as shown in FIG. 3C. The straight line X=t for determining the area under the curve may be determined to be different as necessary and used as an element for determining a threshold value which will be described below.

When the time-blood glucose graph is generated, the prediction model construction unit 120 may calculate an area under the curve (AUC) from the generated time-blood glucose graph and construct a prediction model on the basis of a correlation between the acquired near-infrared spectral data and the calculated area under the curve.

The prediction model construction unit 120 may construct a disease prediction model for determining the correlation using the near-infrared spectral data as an independent variable of a preset regression analysis algorithm and the generated time-blood glucose graph as a dependent variable. For example, when the correlation is determined using the spectral data of the subject as the independent variable and the time-blood glucose graph of the same subject as the dependent variable, the dependent variable may be predicted from the independent variable on the basis of a change in the dependent variable according to a change in the independent variable. In this case, the regression analysis algorithm may include, for example, a partial least square regression algorithm, a principal components regression algorithm, or a multivariate regression algorithm but is not limited thereto.

FIG. 4 is an illustrative diagram illustrating a process of establishing a disease prediction model according to an exemplary embodiment. Referring to FIG. 4 illustrating a process of establishing a disease prediction model, the preprocessed near-infrared spectral data and the area under the curve of the time-blood glucose graph are respectively used as an independent variable and a dependent variable.

The spectral data acquisition unit 110 may acquire the near-infrared spectral data of the subject, the preprocessing unit 210 may perform preprocessing by applying a first-order Savitzky-Golay derivative filter, and the prediction model construction unit 120 may establish the disease prediction model using the preprocessed spectral data as an independent variable and the area under the curve of the time-blood glucose graph of the same subject as a dependent variable. In this case, referring to FIG. 4, the area under the curve may be an area of a portion surrounded by a curve drawn in the time-blood glucose graph, X-axis, Y-axis, and a straight line graph of X=2. Further, the area under the curve based on the time-blood glucose graph rather than the time-blood glucose graph may be applied to establish the disease prediction model.

Referring back to FIG. 2, the feature information input unit 240 may receive feature information such as sex, age, height, body weight, and disease history of the subject.

For example, the prediction model construction unit 120 may construct a prediction model in one or more groups on the basis of the input feature information of the subject. For example, when the sex is input as the feature information, the prediction model construction unit 120 may construct the prediction model without distinguishing between a man and a woman or may construct the prediction model with distinguishing between a man and a woman by reflecting the input feature information.

As another exemplary example, when sex and age are input as the feature information, the prediction model construction unit 120 may construct the prediction model according to sex and re-classify the prediction model according to age. This classification of the prediction model may be made using each of the pieces of the input feature information or a combination of them. The input of the feature information and the classification of the input model may be designated by a user in consideration of a type and expression characteristics of the disease.

Figure 5:
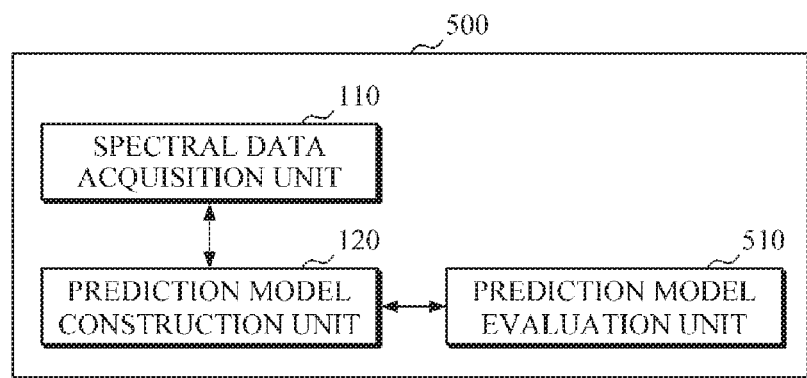
FIG. 5 is a block diagram illustrating a disease prediction model construction apparatus according to still another exemplary embodiment.

FIG. 5 is a block diagram illustrating a disease prediction model construction apparatus according to another exemplary embodiment. As illustrated, the disease prediction model construction apparatus 500 may further include a prediction model evaluation unit 510 in addition to the spectral data acquisition unit 110 and the prediction model construction unit 120 that are constituents of the disease prediction model construction apparatus 100 of FIG. 1. However, this is only illustrative. The disease prediction model construction apparatus 500 in this exemplar embodiment may further include the configuration of the disease prediction model construction apparatus 200 according to the embodiment in FIG. 2, and the present exemplary embodiment is not particularly limited to any of the embodiments. Hereinafter, a different configuration will be mainly described.

The prediction model evaluation unit 510 may verify or evaluate the constructed prediction model. For example, when the prediction model construction unit 120 acquires the near-infrared spectral data for a plurality of subjects and constructs the disease prediction model using the acquired near-infrared spectral data of the plurality of subjects and the area under the curve of the time-blood glucose graph of the same subjects as described above, the prediction model evaluation unit 510 may predict the area under the curve for a preset number of subjects using the disease prediction model constructed by the prediction model construction unit 120 and compare the predicted area under the curve with an area under the curve actually measured for the preset number of subjects to verify the construed disease prediction model.

In this case, the prediction model evaluation unit 510 may determine a coefficient of correlation (R value) of an actually measured area under the curve and the predicted area under the curve. The prediction model evaluation unit 501 may determine that the constructed disease prediction model is suitable when the determined coefficient of correlation satisfies a preset criterion.

Further, when the constructed prediction model is determined not to be suitable for disease prediction, the prediction model evaluation unit 510 may cause the spectral data acquisition unit 110 to re-acquire the spectral data or may change the application algorithm of the preprocessing unit 210 or the prediction model construction unit 120. The evaluation of the prediction model may be based on a coefficient of correlation (R), a coefficient of determination ($R^2$), a regression line, a slope (slope value) of the regression line, or the like, but the present exemplary embodiment is not limited thereto.

Figure 6:
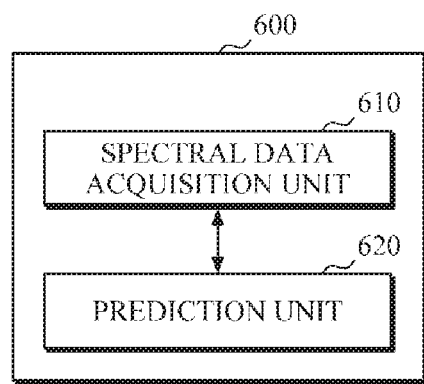
FIG. 6 is a block diagram illustrating a disease prediction apparatus according to an exemplary embodiment.

FIG. 6 is a block diagram illustrating a disease prediction apparatus according to an exemplary embodiment. The disease prediction apparatus 600 may include a spectral data acquisition unit 610 and a prediction unit 620.

The spectral data acquisition unit 610 may emit near-infrared rays toward the skin of a subject to acquire near-infrared spectral data that is carried by the near-infrared rays reflected from the skin. In this case, a near-infrared spectral region may have a wavelength range from 1158 nm to 2130 nm but is not limited thereto. Further, a measured part of the subject is not limited to a specific part of a body and may be changed according to convenience and physical condition of the subject.

The spectral data acquisition unit 610 may acquire the near-infrared spectral data of the subject in a measurement. Alternatively, the spectral data acquisition unit 610 may acquire the near-infrared spectral data in several measurements. In this case, the spectral data acquisition unit 610 may acquire statistical values including an average value, a median value, a minimum value, a maximum value, etc. of a plurality of acquired spectral data as the near-infrared spectral data of the subject. However, the present exemplary embodiment is not limited thereto, and each of the measured spectral data items may be weighted and a resultant statistical value may be acquired as the near-infrared spectral data of the subject.

When the near-infrared spectral data of the subject is acquired, the prediction unit 620 may predict the disease of the subject by applying a disease prediction model to the acquired spectral data of the subject. For example, the prediction unit 620 may estimate an area under a curve (AUC) of the time-blood glucose graph corresponding to the near-infrared spectral data of the subject acquired from the spectral data acquisition unit 610 using the disease prediction model and compare the estimated area under the curve with a threshold value to predict the disease of the subject. Here, the disease may include an impaired glucose tolerance which is one of the prediabetes symptoms but is not limited thereto.

The threshold value of the prediction unit 620 is preset according to a predetermined criterion including the time of the time-blood glucose graph. The threshold value may be initially set by the user or may be updated over a wired or wireless network. For example, the time-blood glucose graph may be generated using a method of collecting blood at certain time intervals for two hours after the subject takes glucose of 75 g in a fasting state and a change in a concentration of the glucose from the collected blood in a step of measuring a change in the blood glucose may be tracked. In this case, when the threshold value is initially set so that the disease is predicted as an impaired glucose tolerance when the area under the curve of the time-blood glucose graph is greater than or equal to 290 mg·h/dl, the prediction unit 620 compares the estimated area under the curve for the subject with the threshold value. When the estimated area under the curve for the subject is greater than or equal to 290 mg·h/dl, the prediction unit 620 may predict that the subject suffers from the impaired glucose tolerance. When an end of a time to measure a change in the blood glucose is changed in the generation of the time-blood glucose graph or when a reference time (t) is changed in a calculation of the area under the curve, a user or an operator may change an initial setting of the threshold value. Further, when information on the time is reflected in the disease prediction model, the prediction unit 620 may update the threshold value over a wire or wireless network.

Figure 7:
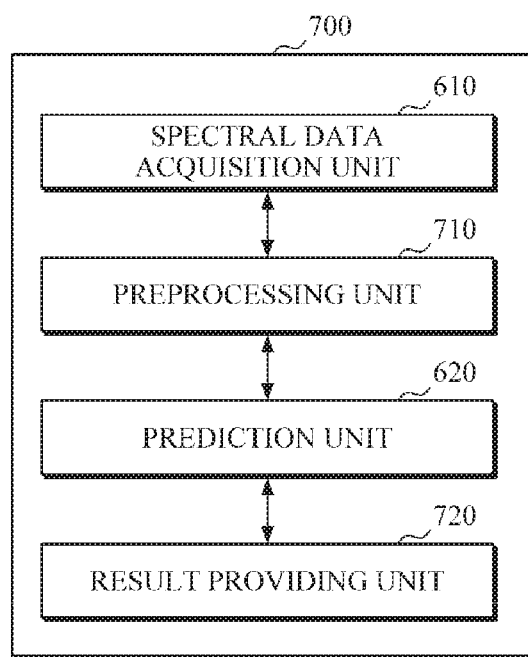
FIG. 7 is a block diagram illustrating a disease prediction apparatus according to another exemplary embodiment.

FIG. 7 is a block diagram illustrating a disease prediction apparatus according to another embodiment. As illustrated, the disease prediction apparatus 700 may include a spectral data acquisition unit 610, a preprocessing unit 710, a prediction unit 620, and a result providing unit 720. Hereinafter, a different configuration will be mainly described.

The preprocessing unit 710 may preprocess the near-infrared spectral data acquired from the subject to remove noise from the acquired data. In this case, in the preprocessing method, a moving average filter, an average value filter, a weighting value filter, or a Savitzky-Golay filter may be used.

For example, the same preprocessing method as the preprocessing method used to construct the disease prediction model may be used. For example, referring to FIG. 3B, a result of the preprocessing with a first-order Savitzky-Golay derivative filter is illustrated. This preprocessing process may be used to remove noise and minimize error according to characteristics of the skin of the subject and error generated according to a measured part.

The result providing unit 720 may compare the area under the curve estimated for the subject with a threshold value to provide a prediction result. For example, when the threshold value is initially set so that the disease is predicted as the impaired glucose tolerance when the area under the curve of the time-blood glucose graph is greater than or equal to 290 mg·h/dl, the area under the curve estimated for the subject is compared with the threshold value. When the area under the curve is greater than or equal to the threshold value or less than the threshold value, a result thereof may be provided using at least one of a visual method (for example, an LCD screen or a lamp), an auditory method (for example, a speaker), and a tactile method (for example, vibration).

Figure 8:
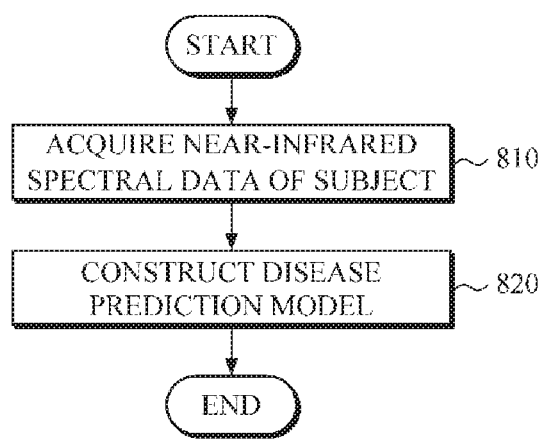
FIG. 8 is a flowchart of a disease prediction model construction method according to an exemplary embodiment.

FIG. 8 is a flowchart of a disease prediction model construction method according to an embodiment. The disease prediction model construction method according to an embodiment may be performed by the disease prediction model construction apparatus 100.

The disease prediction model construction apparatus 100 may near-infrared rays toward the skin of a subject to acquire near-infrared spectral data of the subject (operation 810).

For example, the disease prediction model construction apparatus 100 may emit the near-infrared rays to the skin of the subject and sense light that is reflected from the skin, for example reflected or transmitted light, to acquire the near-infrared spectral data (operation 810). In this case, a near-infrared spectral region may be a region in a wavelength range from 1158 nm to 2130 nm but is not limited thereto. Further, a measured part of the subject is not limited to a specific part of a body and may be changed according to convenience and physical condition of the subject.

The disease prediction model construction apparatus 100 may acquire the near-infrared spectral data of the subject in a measurement (operation 810). Alternatively, the disease prediction model construction apparatus 100 may acquire the near-infrared spectral data in several measurements. In this case, the disease prediction model construction apparatus 100 may acquire statistical values including an average value, a median value, a minimum value, a maximum value, etc. of a plurality of acquired spectral data as the near-infrared spectral data of the subject. However, the present exemplary embodiment is not limited thereto, and each of the measured spectral data items may be weighted, and the resultant statistical value may be acquired as the near-infrared spectral data of the subject. In this case, the number of subjects is not particularly limited, and when there is a plurality of subjects, the disease prediction model construction apparatus 100 may acquire the near-infrared spectral data for each subject.

Then, the disease prediction apparatus 100 may construct the disease prediction model based on the time-blood glucose graph generated for the subject and the acquired near-infrared spectral data of the subject (operation 820).

The disease prediction model construction apparatus 100 may construct a disease prediction model for disease prediction using the acquired near-infrared spectral data of the subject (operation 820). For example, the disease prediction model construction apparatus 100 may construct the disease prediction model on the basis of the near-infrared spectral data acquired for the subject and the time-blood glucose graph generated for the subject (operation 820). Here, the disease may include impaired glucose tolerance which is one of the prediabetes symptoms but is not limited thereto.

For example, the disease prediction model construction apparatus 100 may calculate an area under a curve using the time-blood glucose graph generated for the subject and construct the disease prediction model using a correlation between the near-infrared spectral data acquired for the subject and the calculated area under the curve. For example, when the spectral data of the subject is used as an independent variable and the time-blood glucose graph of the same subject is used as a dependent variable to determine a correlation, the dependent variable may be predicted from the independent variable on the basis of a change in the dependent variable according to a change in the independent variable. In this case, the regression analysis algorithm may include, for example, a partial least square regression algorithm, a principal components regression algorithm, or a multivariate regression algorithm but is not limited thereto.

Figure 9:
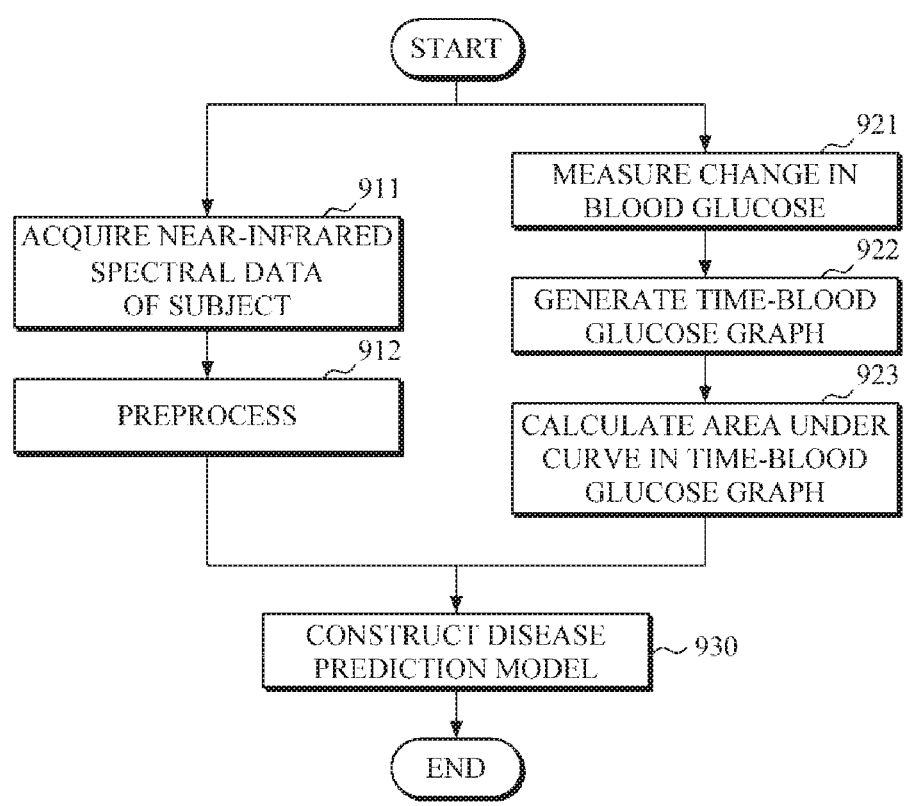
FIG. 9 is a flowchart illustrating a method of constructing disease prediction model according to another exemplary embodiment.

FIG. 9 is a flowchart illustrating a disease prediction model construction method according to another embodiment. The disease prediction model construction method according to an exemplary embodiment may be performed by the disease prediction model construction apparatus 200 in FIG. 2. Hereinafter, a new configuration will be mainly described.

The disease prediction model construction apparatus 200 may emit near-infrared rays toward the skin of a subject to acquire near-infrared spectral data of the subject (operation 911).

For example, the disease prediction model construction apparatus 200 may emit the near-infrared rays to the skin and sense light that is incident from the skin, for example reflected, deflected, or refracted light, to acquire the near-infrared spectral data. A measured part of the subject is not limited to a specific part of a body and may be changed according to convenience and physical condition of the subject.

Further, the disease prediction model construction apparatus 200 may acquire the near-infrared spectral data of the subject in a measurement or may acquire the near-infrared spectral data in several measurements (operation 911).

Then, the disease prediction model construction apparatus 200 may preprocess the spectral data acquired from the subject to remove noise from the acquired data (operation 912). For example, through the preprocessing process, it is possible to remove noise of the acquired spectral data of the subject and minimize a deviation according to characteristics of the skin between the subjects and a deviation generated according to measured part.

In this case, a preprocessing algorithm may include, for example, a moving average filter, an average value filter, a weighting value filter, and a Savitzky-Golay filter, but the present exemplary embodiment is not limited thereto.

Then, the disease prediction model construction apparatus 200 may measure a change in the blood glucose for a predetermined time from the subject taking glucose in a fasting state (operation 921). For example, the disease prediction model construction apparatus 200 may measure the change in the blood glucose by tracking a change in a concentration of glucose from the blood collected at certain time intervals for two hours after the subject takes glucose of 75 g in a fasting state in step 921. For example, the disease prediction model construction apparatus 200 may measure the change in the blood glucose by an oral glucose tolerance test (OGTT).

Then, the disease prediction model construction apparatus 200 may generate the time-blood glucose graph on the basis of the measured change in the blood glucose (operation 922). For example, since the concentration of the glucose in the blood immediately after the subject takes the glucose of 75 g varies with time, the disease prediction model construction apparatus 200 may obtain a blood glucose graph on a two-dimensional plane with a change in the time as X-axis and the blood glucose according to time as Y-axis by tracking the glucose concentration of the blood collected at certain time intervals according to time.

Then, the disease prediction model construction apparatus 200 may calculate the area under a curve which is drawn in the time-blood glucose graph (operation 923). For example, the disease prediction model construction apparatus 200 may calculate an area (mg·h/dl) of a portion surrounded by the curve drawn in the time-blood glucose graph, X-axis, Y-axis, and a straight line (X=t) for arbitrary time t. In this case, the straight line X=t for determining the area under the curve may be determined to be different as necessary and used as an element for determining a threshold value. For example, the area under the curve y=f(x) between x=a and x=b may be obtained by integrating y=f(x) between the limits of a and b. Here, the values of a and b may be set as 0.0 and 2.0 as shown in FIGS. 3C and 4.

Then, the disease prediction model construction apparatus 200 may construct the disease prediction model on the basis of a correlation between the acquired near-infrared spectral data and the calculated area under the curve (operation 930). For example, the disease prediction model construction apparatus 200 may determine the correlation using the near-infrared spectral data as an independent variable of a preset regression analysis algorithm and the generated time-blood glucose graph as a dependent variable. For example, when the correlation is determined using the spectral data of the subject as the independent variable and the time-blood glucose graph of the same subject as the dependent variable, the dependent variable may be predicted from the independent variable on the basis of a change in the dependent variable according to a change in the independent variable.

In this case, the regression analysis algorithm used to construct the disease prediction model may include, for example, a partial least square regression algorithm, a principal components regression algorithm, or a multivariate regression algorithm but is not limited thereto.

Further, a series of processes for acquiring and preprocessing the near-infrared spectral data of the subject and a series of processes for measuring the change in the blood glucose, generating the time-blood glucose graph, and calculating the area under the curve in the time-blood glucose graph in the disease prediction model construction apparatus 200 are not performed in a particularly determined order and may be changed according to condition or an operating intention of the subject and the user.

Figure 10:
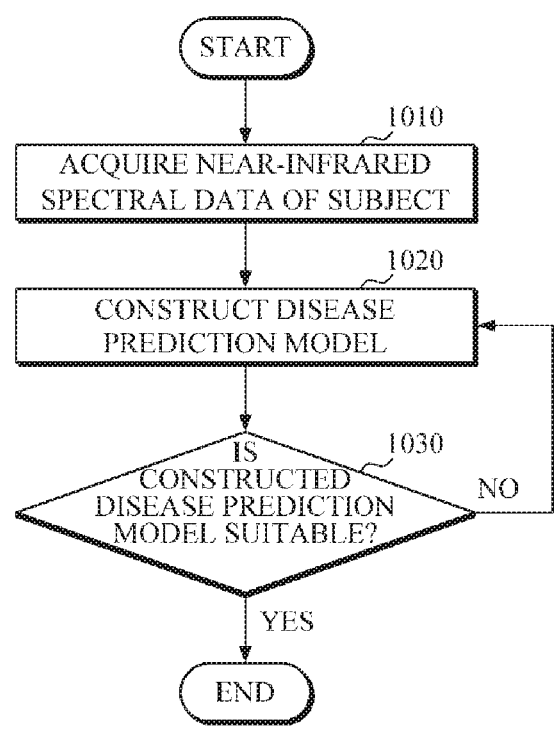
FIG. 10 is a flowchart illustrating a disease prediction model construction method according to still another exemplary embodiment.

FIG. 10 is a flowchart illustrating a disease prediction model construction method according to another embodiment. The disease prediction model construction method according to an embodiment may be performed by the disease prediction model construction apparatus 500 in FIG. 5. Hereinafter, a new configuration will be mainly described.

The disease prediction model construction apparatus 500 may verify or evaluate the constructed prediction model (operation 1030). For example, when the disease prediction model construction apparatus 500 acquires the near-infrared spectral data for a plurality of subjects (operation 1010) and constructs the disease prediction model using the acquired near-infrared spectral data of the plurality of subjects and the area under the curve of the time-blood glucose graph of the same subjects as described above (operation 1020), the disease prediction model construction apparatus 500 may predict the area under the curve for a preset number of subjects using the constructed disease prediction model and compare the predicted area under the curve with an actually measured area under the curve to verify the constructed disease prediction model (operation 1010). For example, the disease prediction model construction apparatus 500 may determine a coefficient of correlation (R value) of an actually measured area under the curve and the predicted area under the curve and evaluate that the constructed disease prediction model is suitable when the determined coefficient of correlation satisfies a preset criterion.

Further, when the constructed prediction model is determined not to be suitable for disease prediction, the disease prediction model construction apparatus 500 may re-acquire the near-infrared spectral data of the subject or change a preprocessing application algorithm or an application algorithm for construction of a disease prediction model. For example, the disease prediction model construction apparatus 500 may predict the area under the curve using the disease prediction model constructed for the preset number of subjects and compare the predicted area under the curve with an area under a curve actually measured for preset subjects to verify the constructed disease prediction model.

In this case, when the constructed disease prediction model is determined not to be suitable for disease prediction, the disease prediction model construction apparatus 500 may reconstruct the disease prediction model, and the disease prediction model construction apparatus 500 may apply a regression analysis algorithm other than the regression analysis algorithm first used to construct the disease prediction model in step 1020 to construct the disease prediction model.

However, this is illustrative, and the present exemplary embodiment is not limited thereto. The disease prediction model construction apparatus 500 may re-acquire the spectral data of the subject or change the preprocessing application algorithm. The present exemplary embodiment is not particularly limited to any one of the embodiments. In this case, the evaluation of the prediction model is based on a coefficient of correlation (R), a coefficient of determination ($R^2$), a regression line, a slope (slope value) of the regression line, or the like, but the present exemplary embodiment is not limited thereto.

Figure 11:
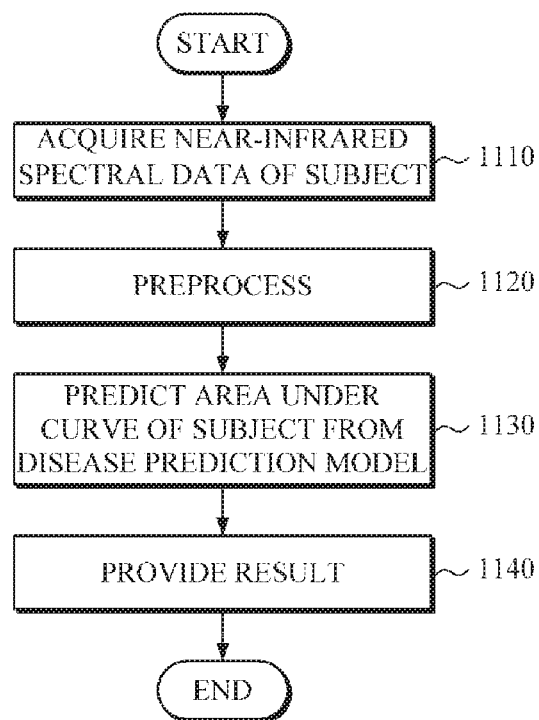
FIG. 11 is a flowchart illustrating a method of predicting a disease according to an exemplary embodiment.

FIG. 11 is a flowchart illustrating a method of predicting a disease according to an embodiment. The method of predicting disease according to an embodiment may be performed by the disease prediction apparatus 700 in FIG. 7.

The disease prediction apparatus 700 may emit near-infrared rays toward the skin of a subject to acquire near-infrared spectral data (operation 1110). For example, the disease prediction apparatus 700 may emit the near-infrared rays to the skin and sense light that is incident from the skin, for example reflected, deflected, and/or refracted light, to acquire the near-infrared spectral data (operation 1110). Further, a measured part of the subject is not limited to a specific part of a body and may be changed according to convenience and a physical condition of the subject.

Further, in the acquisition (operation 1110) of the near-infrared spectral data of the subject, the near-infrared spectral data of the subject may be acquired in a measurement, or the near-infrared spectral data of the subject may be acquired in several measurements.

Then, the disease prediction apparatus 700 may preprocess the spectral data (operation 1110) acquired from the subject to remove noise from the acquired data (operation 1120).

For example, the disease prediction apparatus 700 may use the same preprocessing method as the preprocessing method used to construct the disease prediction model to be compatible with the generated disease prediction model. Further, by the preprocessing process (operation 1120), it is possible to remove noise and minimize error according to characteristics of the skin of the subject and error generated according to a measured part.

Then, the disease prediction apparatus 700 may predict an area under the curve of the graph for the acquired near-infrared spectrum (operation 1110) for the subject (operation 1130).

For example, the disease prediction apparatus 700 may estimate an area under the curve (AUC) of the time-blood glucose graph corresponding to the acquired near-infrared spectral data of the subject and use the estimate area under the curve as an area under the curve of the time-blood glucose graph for the subject.

Further, although not illustrated, the disease prediction apparatus 700 may receive feature information such as sex, age, height, body weight, or disease history of the subject. For example, when the disease prediction model is constructed with the feature information on the sex of the subject, the disease prediction apparatus 700 may reflect the input feature information and predict the area under the curve of the subject from the disease prediction model (operation 1130).

Then, the disease prediction apparatus 700 may compare the estimated area under the curve of the subject with the threshold value to predict the disease of the subject. Here, the disease may include an impaired glucose tolerance which is one of the prediabetes symptoms but is not limited thereto.

The threshold value of the disease prediction apparatus 700 is preset according to a predetermined criterion including time of the time-blood glucose graph. For example, the threshold value may be initially set by the user or may be updated over a wired or wireless network.

For example, the disease prediction apparatus 700 initially sets the threshold value to 290 mg·h/dl so that there is an impaired glucose tolerance when the calculated area under the curve of the time-blood glucose graph is greater than or equal to 290 mg·h/dl. In this case, the disease prediction apparatus 700 may compare the estimated area under the curve for the subject with the threshold value and predict that the subject suffers from the impaired glucose tolerance when the estimated area under the curve for the subject is greater than or equal to 290 mg·h/dl.

Further, in the disease prediction apparatus 700, when an ending time for measuring a change in the blood glucose is changed in generation of the time-blood glucose graph, a user or an operator may change an initial setting of the threshold value. Further, when information on the time is reflected in the disease prediction model, the threshold value may be updated over a wire or wireless network.

Then, the disease prediction apparatus 700 may provide a prediction result obtained by comparing the area under the curve estimated for the subject with the threshold value (operation 1140). For example, when the threshold value of the disease prediction apparatus 700 is initially set so that the disease is predicted as the impaired glucose tolerance when the area under the curve of the time-blood glucose graph is greater than or equal to 290 mg·h/dl, the area under the curve estimated for the subject is compared with the threshold value. When the area under the curve is greater than or equal to the threshold value or less than the threshold value, a result thereof may be provided using at least one of a visual method (e.g., an LCD screen or a lamp), an auditory method (e.g., a speaker), and a tactile method (e.g., vibration).

While not restricted thereto, the operations or steps of the methods or algorithms according to the above exemplary embodiments may be implemented as computer readable codes on a computer readable record medium. Codes and code segments constituting the computer program can be easily inferred by a skilled computer programmer in the art. The computer readable record medium includes all types of record media in which computer readable data are stored. Examples of the computer readable record medium include a read-only memory (ROM), a random-access memory (RAM), a CD-ROM, a magnetic tape, a floppy disk, and an optical data storage. Further, the record medium may be implemented in the form of a carrier wave such as Internet transmission. In addition, the computer readable record medium may be distributed to computer systems over a network in which computer readable codes may be stored and executed in a distributed manner. Also, the operations or steps of the methods or algorithms according to the above an exemplary embodiments may be written as a computer program transmitted over a computer-readable transmission medium, such as a carrier wave, and received and implemented in general-use or special-purpose digital computers that execute the programs. Moreover, it is understood that in exemplary embodiments, one or more units (e.g., those represented by a block as illustrated in FIGS. 1 and 2) of the above-described apparatuses and devices can include or implemented by circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A disease prediction apparatus comprising:
a spectral data acquisition circuit configured to emit near-infrared rays toward a skin of a subject to acquire near-infrared spectral data; and
a prediction circuit configured to apply a disease prediction model to the acquired spectral data and predict disease of the subject,
wherein the disease prediction model is based on a correlation between near-infrared spectral data acquired for at least one subject as an independent variable and an area under a curve (AUC) of a time-blood glucose graph of the same at least one subject as a dependent variable.

2. The disease prediction apparatus according to claim 1, wherein the disease includes an impaired glucose tolerance.

3. The disease prediction apparatus according to claim 1, further comprising a preprocessing circuit configured to remove noise from the acquired near-infrared spectral data.

4. The disease prediction apparatus according to claim 1, wherein the prediction circuit is further configured to estimate an area under a curve (AUC) of a time-blood glucose graph generated from the acquired near-infrared spectral data based on the disease prediction model and compare the estimated area under the curve with a threshold value to predict the disease.

5. The disease prediction apparatus according to claim 4, wherein the threshold value is preset according to a predetermined criterion including time of the time-blood glucose graph.

6. The disease prediction apparatus according to claim 1, further comprising a result providing circuit configured to provide information of the predicted disease to the subject.

* * * * *